United States Patent
Dickinson

(10) Patent No.: US 8,040,758 B1
(45) Date of Patent: Oct. 18, 2011

(54) GOLF WATCH HAVING HEART RATE MONITORING FOR IMPROVED GOLF GAME

(75) Inventor: Elisabeth Dickinson, Vancouver (CA)

(73) Assignee: Physi-Cal Enterprises LP, Vancouver, BC (CA)

( * ) Notice: Subject to any disclaimer, the term of this patent is extended or adjusted under 35 U.S.C. 154(b) by 847 days.

(21) Appl. No.: 12/108,471

(22) Filed: Apr. 23, 2008

Related U.S. Application Data

(60) Provisional application No. 60/915,115, filed on May 1, 2007.

(51) Int. Cl.
*A61B 5/04* (2006.01)
*G04B 47/06* (2006.01)

(52) U.S. Cl. .............. 368/11; 473/213; 600/509

(58) Field of Classification Search .............. 368/10–11; 473/212–213; 600/509
See application file for complete search history.

(56) References Cited

U.S. PATENT DOCUMENTS

| | | | | |
|---|---|---|---|---|
| 5,738,104 A * | 4/1998 | Lo et al. | | 600/521 |
| 5,890,128 A * | 3/1999 | Diaz et al. | | 705/2 |
| 5,894,454 A * | 4/1999 | Kondo | | 368/11 |
| 6,675,041 B2 * | 1/2004 | Dickinson | | 600/509 |
| 6,950,695 B2 * | 9/2005 | Chen | | 600/509 |
| 7,163,512 B1 * | 1/2007 | Childre et al. | | 600/500 |
| 7,171,259 B2 * | 1/2007 | Rytky | | 600/509 |
| 7,457,201 B2 * | 11/2008 | Jaermann et al. | | 368/10 |
| 7,462,151 B2 * | 12/2008 | Childre et al. | | 600/300 |
| 7,539,084 B2 * | 5/2009 | Berseth | | 368/10 |
| 7,894,888 B2 * | 2/2011 | Chan et al. | | 600/509 |
| 7,959,351 B1 * | 6/2011 | Thorpe | | 368/282 |
| 2005/0054940 A1 * | 3/2005 | Almen | | 600/509 |
| 2007/0056582 A1 * | 3/2007 | Wood et al. | | 128/200.24 |
| 2007/0106132 A1 * | 5/2007 | Elhag et al. | | 600/301 |
| 2008/0071181 A1 * | 3/2008 | Stabler et al. | | 600/509 |
| 2008/0294021 A1 * | 11/2008 | Lin et al. | | 600/301 |
| 2009/0137915 A1 * | 5/2009 | Childre et al. | | 600/515 |
| 2009/0270743 A1 * | 10/2009 | Dugan et al. | | 600/500 |
| 2010/0201500 A1 * | 8/2010 | Stirling et al. | | 340/407.1 |
| 2010/0201512 A1 * | 8/2010 | Stirling et al. | | 340/539.11 |

* cited by examiner

*Primary Examiner* — Sean Kayes

(57) ABSTRACT

A wrist-worn apparatus for monitoring a user's performance while playing golf includes a user input, a processor, a heart rate monitor, a timer, a user input, a display, a processor and a memory for storing a plurality of inputted golf parameters that pertain to a round of golf. The apparatus obtains and displays the user's heart rate, providing feedback on the user's heart rate during a round of golf. In addition, the apparatus can store various inputted golf parameters and compute calculated statistics one or more rounds of golf.

9 Claims, 5 Drawing Sheets

GOLF WATCH HAVING HEART RATE MONITORING FOR IMPROVED GOLF GAME

CROSS-REFERENCES TO RELATED APPLICATIONS

The Present Application claims priority to U.S. Provisional Patent Application No. 60/915,115, filed on May 1, 2007.

STATEMENT REGARDING FEDERALLY SPONSORED RESEARCH OR DEVELOPMENT

Not Applicable

BACKGROUND OF THE INVENTION

1. Field of the Invention

This invention relates to an apparatus and method for monitoring, tracking and improving a person's performance during a golf game. The apparatus is provided in the form of a portable wrist-worn device.

2. Description of the Related Art

Golfers are always looking to improve their golf game. One of the most effective ways to improve one's golf game is to integrate the physical, mental and emotional aspects of the game. Studies suggest that to play to one's greatest potential, one must be physically relaxed and mentally engaged. Some researchers note that the heart rate slows down just before performing a specific task, such as putting, and that elite golfers' heart rates slow down much more than that of beginners. Elite golfers generally display higher attention levels, suggesting a link between heart rate deceleration and focus and performance.

Various companies, such as Polar Electro, CardioSport and Timex, offer heart rate monitors to help users keep track of their heart rate during physical activities. For example, Puolakanaho et al., U.S. Pat. No. 6,361,502, entitled "Non-Invasive Measuring Device with Different Operating Modes," disclose a measuring device to be carried by a user during exercise. The measurement device operates in different modes, including a watch mode, a set mode, and an operating mode. In one embodiment, the measuring device is a heart rate monitor that includes a wireless transmitter, which is attached to the user's chest, and a wireless receiver, which is attached to the user's wrist.

One problem with conventional heart rate monitors, however, is that they require a separate chest strap to transmit heart rate information to the wrist-worn unit. Wearing a chest strap may not appeal to all users, as some may find a chest strap uncomfortable or inconvenient to wear for extended periods of time.

The MioSHAPE™ sports watch from Physi-Cal Enterprises, the owner of the present invention, provides electrocardiogram (ECG) accurate heart rate monitoring without the use of a chest strap. This sports watch further includes a calorie tracking system that can be tailored to the user's personal file. The calorie tracking features of the MioSHAPE™ sports watch are disclosed in Dickinson, U.S. Pat. No. 6,675,041, entitled "Electronic Apparatus and Method for Monitoring Net Calorie Intake," which is hereby incorporated by reference in its entirety.

Redwood et al., U.S. Pat. No. 6,275,996, entitled "Articles with Removable Elements," disclose an article to be worn by a user, such as a glove or watch, that includes removable elements. The removable elements may be health enhancing, comfort enhancing or an electronic component. Redwood et al. disclose that the article may be a golf glove and the electronic component may measure heart rate, blood pressure, distance walked, body temperature, external temperature, time, strokes, and/or the speed of the hand of user, and store information, etc.

In addition to the heart rate, heart rate variability (HRV) may also be used to monitor a person's physiology. HRV refers to the beat-to-beat alterations in heart rate. The normal variability in heart rate, which can be determined from an ECG, or from a pulse wave, is due to the synergistic action of the two branches of the autonomic nervous system (ANS), the sympathetic nervous system and the parasympathetic nervous system. The ANS strives toward balance via neural, mechanical, humoral and other physiological mechanisms in order to maintain cardiovascular (and other bodily system) parameters in their most favorable ranges to facilitate optimal reaction to changing external or internal conditions. For most organs including the heart, the sympathetic nervous system stimulates the organ's functioning, while the parasympathetic nervous system inhibits function of that organ. An increase in sympathetic stimulation causes an increase in heart rate. In contrast, an increase in parasympathetic stimulation causes a decrease in heart rate. At rest, both the sympathetic and parasympathetic systems are active with parasympathetic dominance. The actual balance between them changes constantly in an attempt to achieve optimum considering all internal and external stimuli.

HRV may be measured using various time domain or frequency domain methods. Originally, HRV was assessed manually from calculation of the mean R-R interval and its standard deviation measured on short term ECGs. The smaller the standard deviation in R-R intervals, the lower the HRV. Recent developments in microprocessor technology have enabled the calculation of frequency measures based on mathematical manipulations performed on the same ECG-derived data. Further details regarding the various methods of measuring HRV are disclosed in the 1996 article, entitled "Heart Rate Variability: Standards of Measurement, Physiological Interpretation, and Clinical Use" by the Task Force of the European Society of Cardiology the North American Society of Pacing Electrophysiology.

None of the above-mentioned devices, however, discloses a golf-specific watch that is capable of the following: (1) monitoring heart rate and/or HRV to improve a user's control, accuracy and consistency; (2) enabling the user to input and store information relevant to a round of golf, including the number of strokes and putts; and (3) calculating, based on the user-input information, statistics for the round of golf.

SUMMARY OF THE INVENTION

The present invention discloses a golf-specific watch that provides for heart rate and/or HRV monitoring. The watch includes a user input that allows the user to enter and store various golf parameters, such as golf course information and the number of strokes and putts for each hole during a round of golf. The watch also computes and displays to the user statistics for each round of golf, such as an over/under score for a front half, back half or full round of golf, an average number of putts per hole, and a fairway percentage.

In accordance with one embodiment of the invention, a wrist-worn apparatus for monitoring a user's performance during a round of golf on a golf course includes a housing, a strap, a user input, a processor located in the housing, a heart rate monitor, a timer located in the housing and connected to the processor, a memory located in the housing and accessible to the processor, and a display. The strap, which is attached to the housing, secures the apparatus to the user's wrist. The user input is provided on the housing and connected to the processor. The user input enables the user to enter a plurality of golf parameters pertaining to the round of golf. The inputted golf parameters are stored in the memory of the apparatus, where they are accessible to the processor. The heart rate monitor, which is also connected to the processor, includes a plurality of sensors that that are exposed on the housing. The display is located on the housing and connected to the processor, such that the processor can present on the display a heart rate of the user. The processor can also compute and present on the display at least one calculated statistic for the round of golf. The processor may further monitor and compute, using information from the heart rate monitor, a heart rate variability for the user and present on the display an indicator of when the user has achieved a balance between the user's sympathetic and parasympathetic nervous systems.

In accordance with another embodiment of the invention, a method for improving a user's performance during a round of golf on a golf course includes providing a wrist-worn apparatus having a user input, a processor, a heart rate monitor, a timer, a memory and a display. The method further includes periodically monitoring the Having briefly described the present invention, the above and further objects, features and advantages thereof will be recognized by those skilled in the pertinent art from the following detailed description of the invention.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

DETAILED DESCRIPTION OF THE INVENTION

Figure 1:
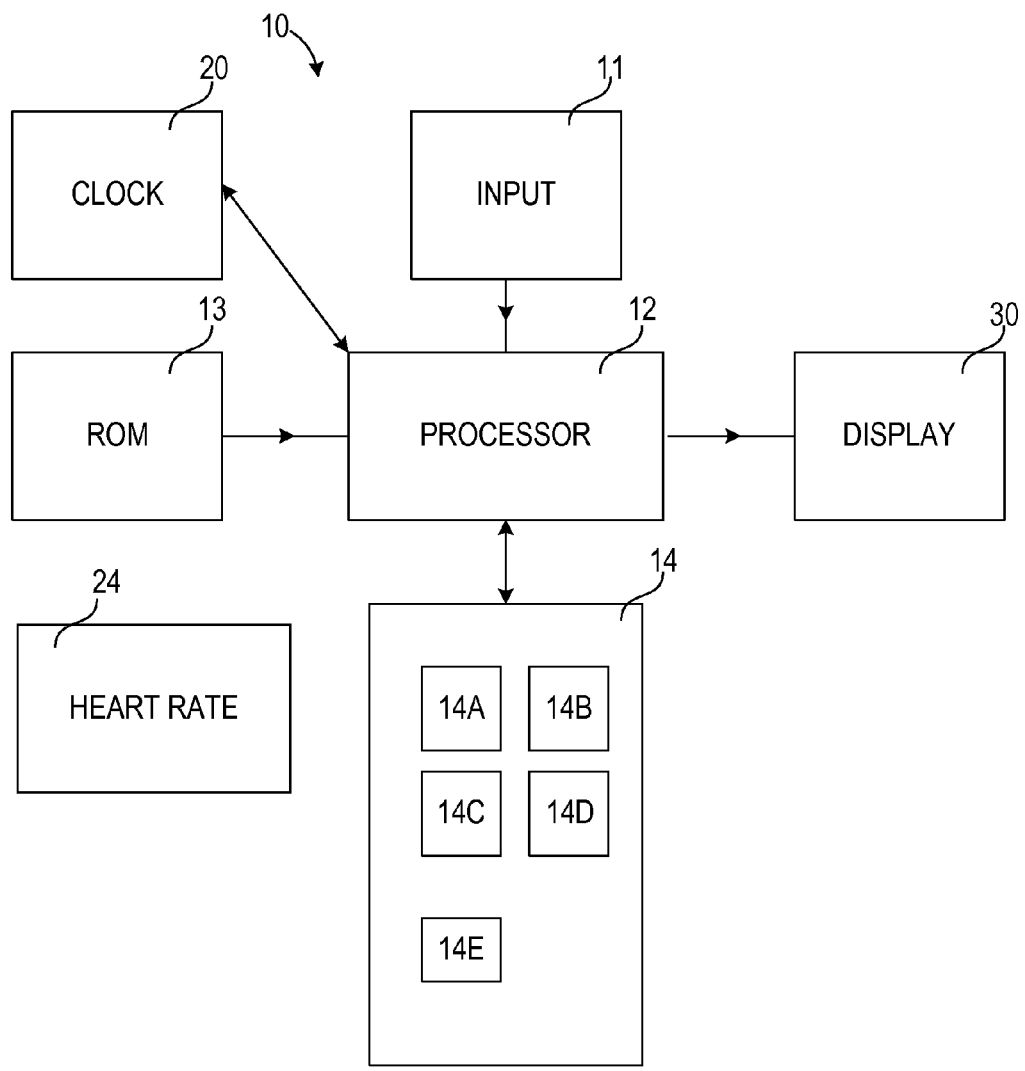
FIG. 1 is a functional block diagram of an apparatus according to the present invention.
Figure 2:
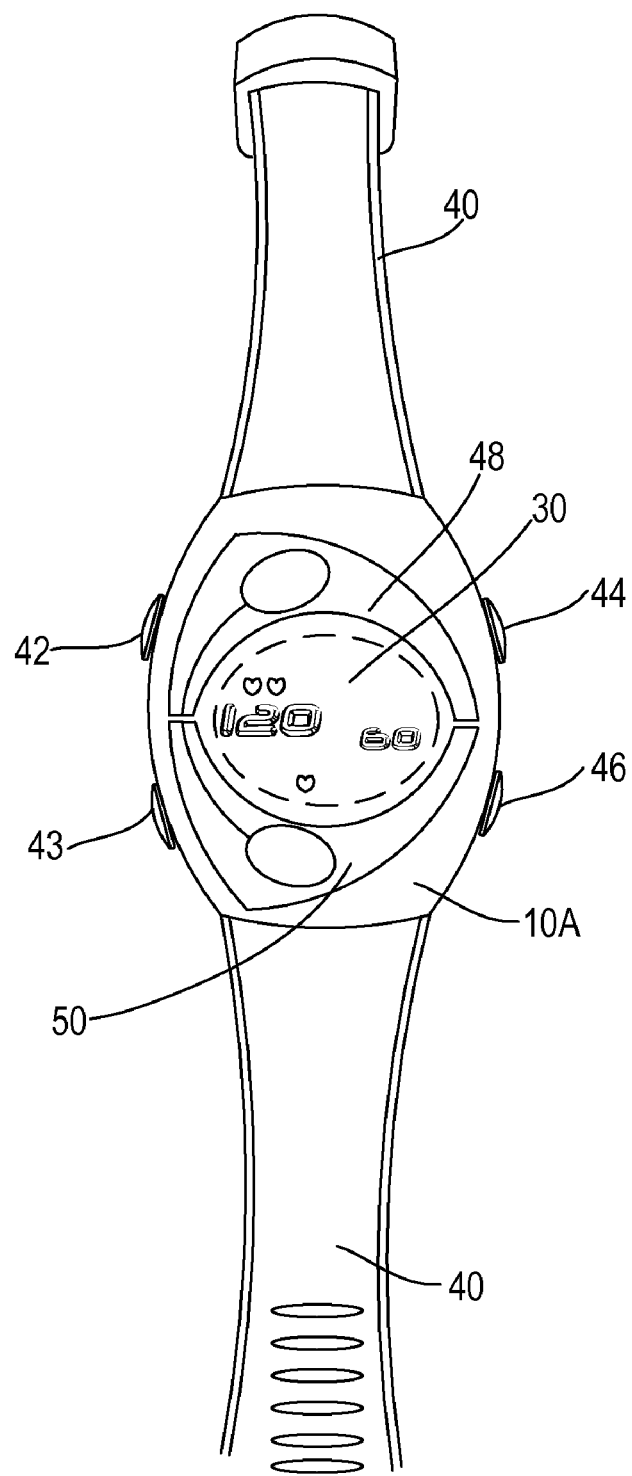
FIG. 2 is a perspective view of an apparatus according to a preferred embodiment of the invention.

FIG. 1 shows a functional block diagram of an apparatus 10 according to the present invention. Apparatus 10 is provided in the form of a compact, portable, self-contained package. Most preferably, apparatus 10 is a wrist-worn apparatus, similar to a wrist watch. As shown in FIG. 2 apparatus 10 has a strap 40, with which apparatus 10 may be secured to a user's wrist.

Apparatus 10 has a user input 11, which allows a user to set up apparatus 10 as described below and to provide apparatus 10 with data regarding a golf course and the user's round of golf at that golf course. User input 11 may comprise a number of buttons, a keypad, a touch screen, or any other suitable, compact means for entering information into apparatus 10.

The data entered by the user at user input 11 is provided to a processor 12, which operates as directed by a software program stored in ROM 13. Processor 12 may comprise a microprocessor. Processor 12 is preferably a type of microprocessor that is compact and consumes very little power. Various microprocessors designed for use in electronic wristwatches may be used for processor 12. The model 80C51 processor made by Intel is one example of a microprocessor which may be used in apparatus 10.

Processor 12 has access to a memory 14, which processor 12 can store data in and retrieve data from during operation. Memory 14 may have a plurality of memory locations 14A-14E. As the user enters data via user input 11, processor 12 stores the data in a memory location of memory 14. Data entered by the user may include personal information, such as birth month and year, gender, base heart rate, which is indicative of the user's general physiological condition, and weight, as well as various golf parameters described in greater detail below.

Apparatus 10 includes a timer 20 and a heart rate monitor 24, both of which are connected to processor 12. At any time, and particularly during a round of golf, the user can periodically cause heart rate monitor 24 to measure the user's heart rate. Heart rate monitor 24 is preferably of a type which detects a user's heart rate by detecting a signal between the user's wrist and a finger of the user's opposite hand. By way of example only, heart rate monitor 24 may be the type of heart rate monitor described in U.S. Pat. No. 5,738,104, entitled "EKG Based Heart Rate Monitor" or U.S. Pat. No. 5,876,350, entitled "EKG Based Heart Rate Monitor with Digital Filter and Enhancement Signal Processor," both of which are hereby incorporated by reference in their entirety.

Processor 12 can then present the user's heart rate information on a display 30. Display 30 may be any suitable type of graphical display. Display 30 is preferably a liquid crystal display (LCD).

FIG. 2 is a view of an apparatus 10 according to one possible embodiment of the invention. Apparatus 10 has the overall form of a wrist watch. Apparatus 10 has a strap 40 by means of which apparatus 10 may be secured to a user's wrist. Apparatus 10 has a rugged body 10A, which houses display 30, and a pair of contacts 48, 50, which are associated with heart rate monitor 24. The rear face of body 10A forms a third electrical contact, which contacts the user's wrist. Apparatus 10 may be largely constructed using technology that is conventional for the construction of electronic watches. Such technology is not described here in detail because it is well known to those skilled in the art. The following description describes a specific embodiment of the invention illustrated in FIG. 2 as a non-limiting example of how the invention may be practiced.

Apparatus 10 of FIG. 2 has four control buttons 42, 43, 44, and 46, which collectively constitute user input 11. Button 42 may be used to cause processor 12 to change into and out of operating modes, in which various parameters relevant to the operation of apparatus 10, can be set. Button 42 may also control the operation of a lamp for the illumination of display 30. Button 43 may activate various functions, including selecting information in set modes as described below and inputting information into memory 14 (or updating previously stored information). Buttons 44 and 46 may be used for selecting information in set modes of apparatus 10 and controlling a stopwatch. Button 44 increases a selected value and starts the running of the stopwatch, while button 46 decreases a selected value and stops the running of the stopwatch.

Figure 3:
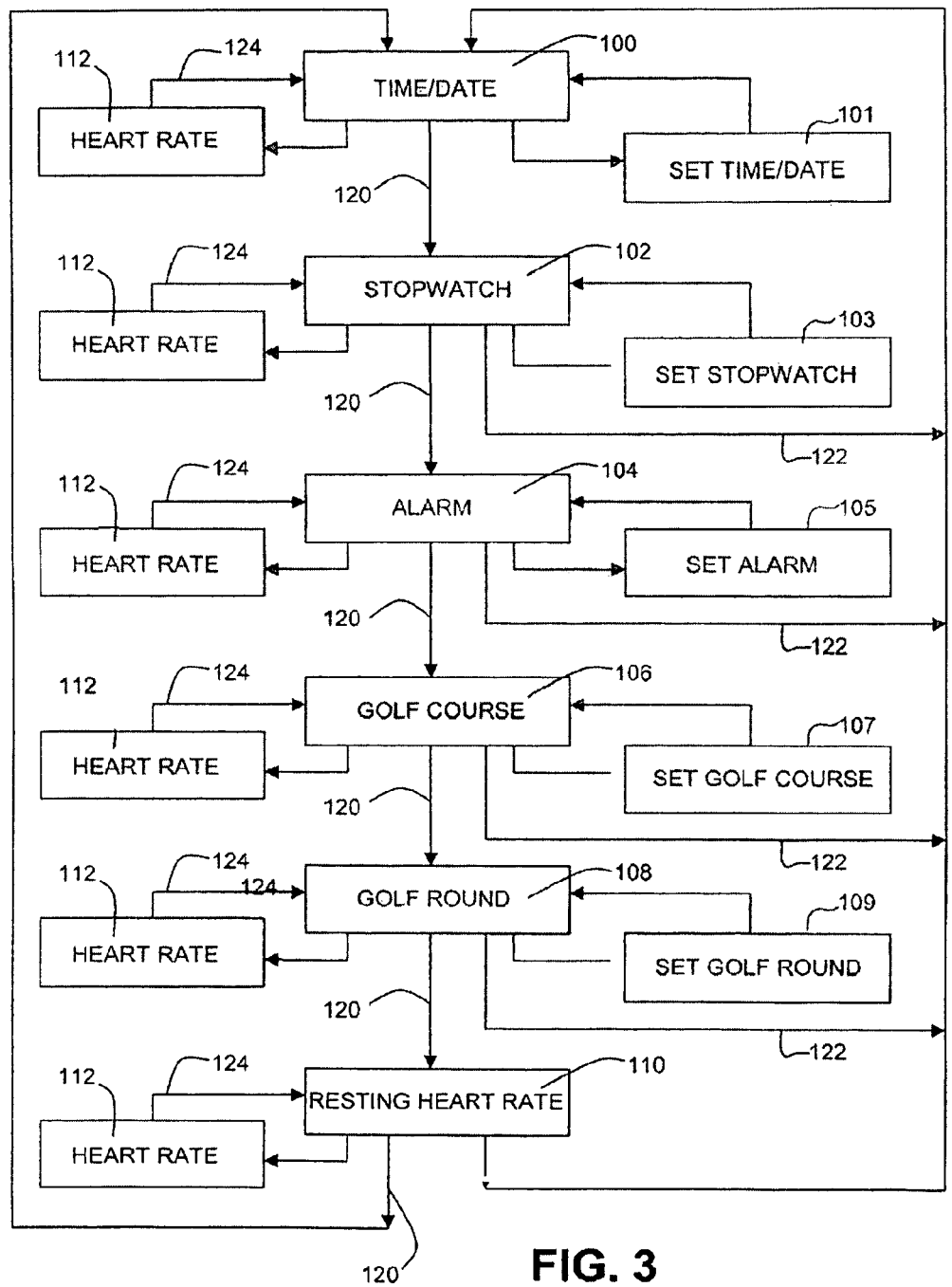
FIG. 3 is a flow chart illustrating various operational modes in the apparatus according to the preferred embodiment of the invention.

FIG. 3 is a flow chart which illustrates various operating modes of apparatus 10. Apparatus 10 has a time/date mode 100, in which the current time and date are displayed on display 30, a stopwatch 102, in which elapsed time is displayed on display 30, an alarm mode 104, in which a time at which an audible, visual or tactile alarm will be set off is displayed on display 30, a golf course mode 106, in which data pertaining to a particular golf course is displayed on display 30, a golf round mode 108, in which data pertaining to a round of golf is displayed on display 30, and a resting heart rate mode 110, in which the user's resting heart rate is displayed on display 30. The user can circulate apparatus 10 through modes 100 to 110 by repeatedly pressing button 42 as indicated by arrows 120. Time/date mode 100 is the default operating mode for apparatus 10. If apparatus 10 is in any of operating modes 102 through 110 and none of buttons 42, 43, 44 or 46 is pressed within a predetermined time interval, then apparatus 10 returns to time/date mode 100 as indicated by arrows 122.

Apparatus 10 may further include additional modes, such as a calorie mode, in which the user's net calorie intake is displayed on display 30, a target mode, in which a user's target net calorie consumption is displayed on display 30, and a weight mode, in which a user's weight, as set by the user, is displayed in display 30, all of which are disclosed in U.S. Pat. No. 6,675,041, entitled "Electronic Apparatus and Method for Monitoring Net Calorie Intake," which is hereby incorporated by reference in its entirety.

Heart rate monitor 24 is activated whenever the user places a finger on each of contacts 48 and 50. Processor 12 is programmed to display the heart rate measured by heart rate monitor 24 on display 30 for a few seconds whenever heart rate monitor 24 completes the measurement of the user's heart rate. The user can thereby measure his or her heart rate at any time. If heart rate monitor 24 fails to detect the user's heart rate then, after a few seconds, apparatus 10 returns to the operating mode it was in before the user activated heart rate monitor 24 as indicated by arrows 124.

Each of operating modes 100 through 108 has a corresponding set mode. For example, mode 100 has a corresponding set mode 101, which allows the user to set the current time and date by manipulating buttons 42, 43, 44 and 46. Such functions are conventional in electronic watches and will not be described here further.

Prior to using apparatus 10 for the first time, the user provides certain information to apparatus 10 through user input 11. This information preferably includes the user's sex, birth month and year (from which the user's age can be calculated), and resting heart rate (as measured by heart rate monitor 24).

Apparatus 10 enables the user to monitor his or her heart rate information while playing golf, store golf-related data during the user's golf game, and later calculate statistics based on that round of golf as well as any previously stored rounds of golf. Heart rate information is a good indicator of the user's emotional and mental state. Apparatus 10 enables the user to monitor his or her physiological state during a round of golf and track the user's progress during the round. In a preferred embodiment, apparatus 10 is capable of storing in memory 14 data for multiple golf courses and multiple rounds of golf, so that the user may track improvements over time.

Figure 4:
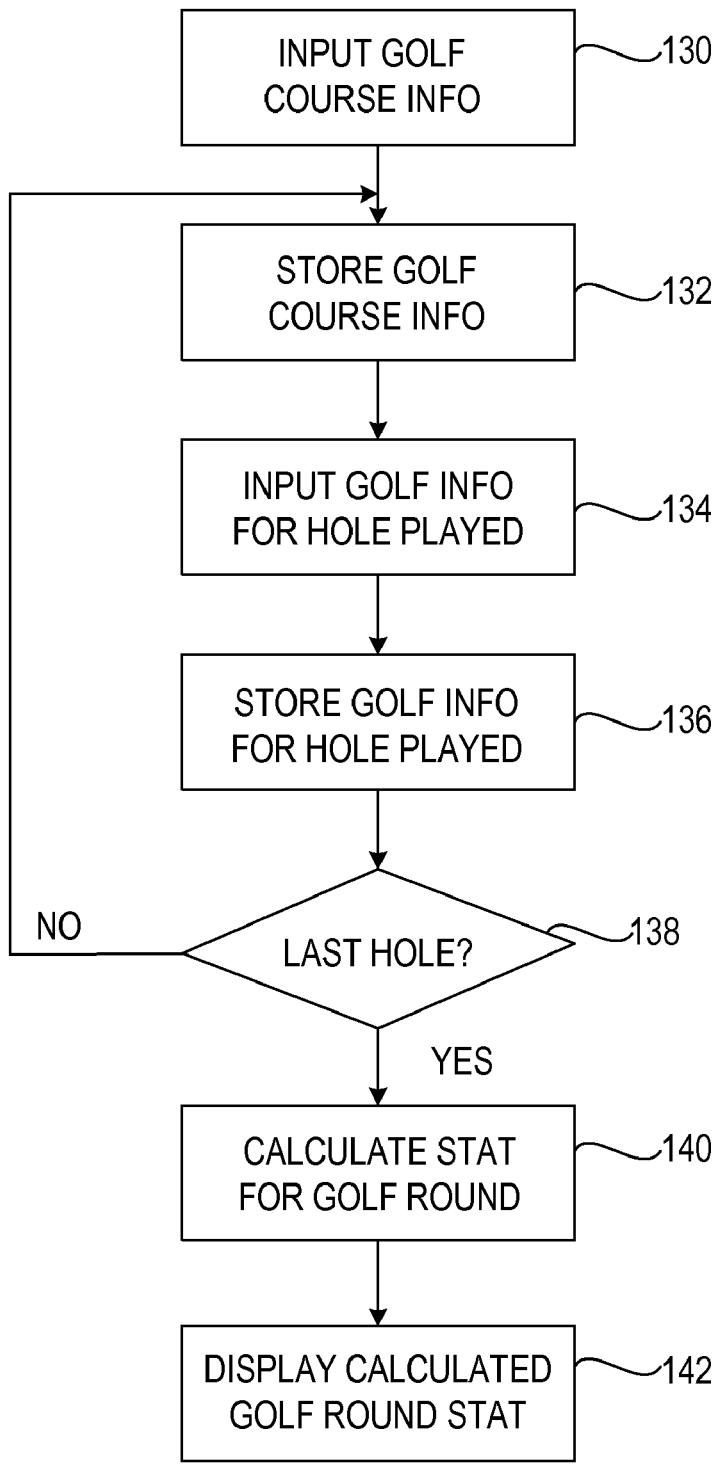
FIG. 4 is a flow chart illustrating a method of calculating statistics for a single round of golf.

FIG. 4 is a flow chart illustrating how the user would utilize apparatus 10 to store a plurality of golf parameters during a round of golf and generate statistics for that round of golf. At step 130, the user would navigate apparatus 10, using user input 42, to present golf course mode 106 on display 30. In golf course mode 106, the user may enter using user inputs 42, 43, 44 and 46 golf parameters related to a particular golf course. Golf parameters relevant to a particular golf course may include the following: golf course rating; slope ratings; and par values for each hole of the golf course. At step 132, data entered into apparatus 10 is stored by processor 12 in suitable memory locations of memory 14.

At step 134, the user would navigate apparatus 10 to present golf round mode 108 on display 30. In golf round mode 108, the user may input golf parameters relevant a particular hole of the round of golf that the user is playing. For example, golf parameters relevant to a particular hole include the following: number of strokes and putts; whether a stroke landed in a fairway, whether a stroke was made from a sand trap; any penalty shots. At step 136, the golf parameters entered by the user are stored in suitable memory locations of memory 14.

At step 138, the user will return to step 134 and repeat steps 134 and 136, entering additional golf parameters for each subsequent hole of that round of golf, until the round is completed. When the user has completed the round of golf, at step 140, processor 12 will retrieve from memory 14 the golf parameters entered by the user during the round of golf and compute various calculated statistics for the round of golf. Calculated statistics for a round of golf may include the following: total number of strokes and putts for a front half, back half or full round of golf; average putts per hole; over/under score for a front half, back half or full round of golf; fairway percentage; greens in regulation; penalty strokes; sand saves; and handicap. Processor 12 then presents on display 30 the calculated statistics.

In addition to calculating and displaying statistics for a single round of golf, processor 12 may calculate average statistics for multiple rounds of golf, based on the golf parameters for those multiple rounds of golf that are stored in memory 14. In a preferred embodiment of the invention, memory 14 may store data for up to twenty rounds of golf and three different golf courses. The user may review these statistics on display 30 and track improvements in his or her golf game.

At any time during a round of golf, the user may obtain heart rate information by placing two fingers of the opposite hand on contacts 48 and 50 of heart rate monitor 24. Apparatus 10 will switch to heart rate mode 112, as described earlier, and present on display 30 the user's heart rate, providing immediate feedback on the user's current physiological state. The user obtains heart rate information prior to teeing off or putting, after a shot, or while walking between holes. By monitoring heart rate information, the user can determine the optimal heart rate for peak golf performance.

Apparatus 10 may provide additional heart rate information aside from just the user's heart rate. Heart rate variability (HRV) is another indicator of a person's physiology. The autonomic nervous system strives toward balance between its two branches, the parasympathetic and the sympathetic nervous systems. At rest, when the heart rate is lower, both the sympathetic and parasympathetic systems are active with increased parasympathetic activity.

Figure 5:
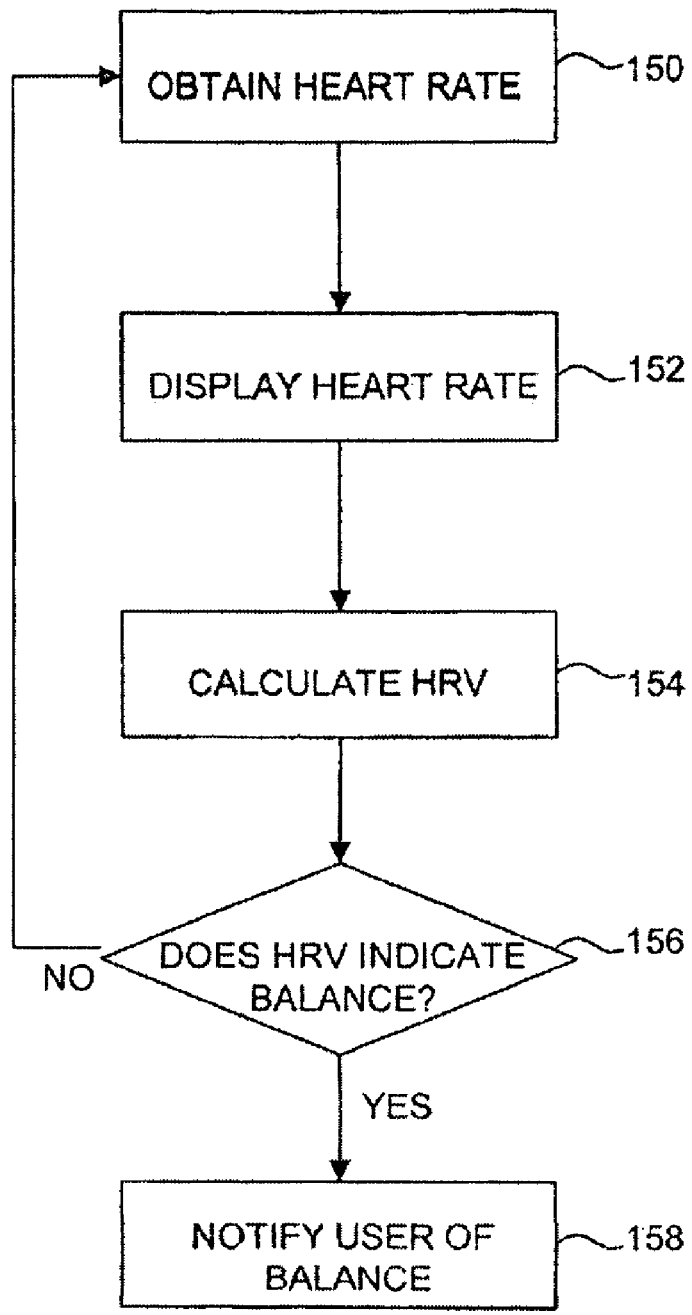
FIG. 5 is a flow chart illustrating a method of notifying a user when his or her parasympathetic and sympathetic nervous systems are in a state of balance.

FIG. 5 is a flow chart illustrating how apparatus 10 incorporates HRV information. At step 150, the user obtains a heart rate reading using heart rate monitor 24. At step 152, processor 12 may display the measured heart rate on display 30. At step 154, processor 12 using pre-programmed algorithms, such as those developed by MedPond LLC, to calculate HRV. Exemplary methods of obtaining physiological data useful with the present invention are disclosed in U.S. Patent Publication Number 2005/0251056, U.S. Patent Publication Number 2005/0251055, U.S. Patent Publication Number 2005/0251054, U.S. Patent Publication Number 2005/0251057, U.S. Patent Publication Number 2005/0251051, U.S. Patent Publication Number 2005/0251424, all of which are hereby incorporated by reference in their entireties.

HRV is a measure of an autonomic function. A thorough discussion of HRV is provided at www.biocomtech.com, which information pertaining to HRV and methods of obtaining and analyzing is hereby incorporated by reference in its entirety. At step 156, processor evaluates whether the HRV indicates an appropriate balance between the parasympathetic and sympathetic nervous systems. If there is not an appropriate balance, apparatus 10 will return to step 150 and obtain another heart rate reading. Apparatus 10 will run through steps 150-154 until the HRV indicates an appropriate balance, signifying that the user is in a relaxed state. At that point, at step 158, processor 12 will provide an indicator on display 30, notifying the user that her or she is in a prime, mental, stress-free state, which is optimal for swinging or putting. The indicator presented on display 30 may be a series of flashing dots, graphical bars or any other visual feedback. In addition, the indicator may be accompanied by an audible sound, such as a series of beeps, such that the user need not focus on display 30 of apparatus 10 in order to determine whether he or she is in an optimal physiological state.

While various embodiments of the present invention have been described above, it should be understood that they have been presented by way of example only, and not of limitation. Thus, the breadth and scope of the present invention should not be limited by any of the above-described exemplary embodiments. Additionally, the invention is described above in terms of various exemplary environments, embodiments and implementations. It should be understood that the various features and functionality described in one or more of the individual embodiments, environments or implementations are not limited in their applicability to the particular environment, embodiment, or implementation with which they are described, but instead can be applied, alone or in some combination, to one or more alternative environments, embodiments or implementations of the invention, whether or not such environments, embodiments or implementations are described and whether or not such features are presented as being a part of a described environment, embodiment, or implementation.

Terms and phrases used in this document, and variations thereof, unless otherwise expressly stated, should be construed as open ended as opposed to limiting. As examples of the foregoing: the term "including" should be read as meaning "including without limitation" or the like; the term "example" is used to provide exemplary instances of the item in discussion, not an exhaustive or limiting list thereof; and terms and phrases such as "known," "apparent to one of skill in the art," "conventional," "traditional," "normal," "standard," and terms and phrases of similar meaning should not be construed as limiting the item described to a given time period or to an item available as of a given time, but instead should be read to encompass conventional, known, apparent, traditional, normal, or standard technologies that may be available now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

I claim as my invention the following:

1. A wristwatch for monitoring a user's performance during a round of golf on a golf course, the golf course having a plurality of holes, the wrist-worn apparatus comprising:
   a housing;
   a strap attached to the housing for securing the housing to the user's wrist;
   a user input on the housing;
   a processor located in the housing and connected to receive information from the user input;
   a heart rate monitor connected to the processor, the heart rate monitor including a plurality of sensors exposed on at least two surfaces of the housing;
   a timer located in the housing and connected to the processor;
   a memory located in the housing and accessible to the processor, the memory including a memory location for storing a plurality of inputted golf parameters, the plurality of inputted golf parameters pertaining to the round of golf;
   a display on the housing, the display being connected to the processor,
   wherein the processor is adapted to present on the display a heart rate of the user, and the processor is adapted to compute and present on the display at least one calculated statistic for the round of golf; the heart rate monitor neither transmits nor receives heart rate information wirelessly; wherein the processor is adapted to compute a heart rate variability from a heart rate obtained by the heart rate monitor; and the processor is adapted to present on the display an indicator of when the user has achieved a balance between the user's sympathetic and parasympathetic nervous systems, the processor determining the balance based upon the user's heart rate variability.

2. The wristwatch according to claim 1, wherein the indicator includes an audible sound notifying the user of the balance between the user's sympathetic and parasympathetic nervous systems.

3. The wristwatch according to claim 1, wherein the plurality of sensors of the heart rate monitor include first and second sensors located on a front surface of the housing and a third sensor located on a rear surface of the housing, the third sensor adapted to be in contact with the user's wrist, the first and second sensors adapted to be contacted by first and second fingers of the user's opposite hand.

4. The wristwatch according to claim 1, wherein the plurality of inputted golf parameters includes a number of strokes and a number of putts for each hole of the round of golf on the golf course.

5. The wristwatch according to claim 1, wherein the at least one calculated statistic for the round of golf includes at least one of: (a) a total number of strokes and a total number of putts for a portion of the round of golf, the portion of the round of golf including at least two holes of the golf course; (b) a total number of strokes and a total number of putts for an entire round of golf on the golf course; and (c) an average number of putts per hole.

6. The wristwatch according to claim 4, wherein the plurality of inputted golf parameters further includes at least one of: (a) a golf course rating; (b) a slope rating for each hole of the golf course; and (c) a par value for each hole of the golf course.

7. The wristwatch according to claim 6, wherein the at least one calculated statistic for the round of golf includes at least one of: (a) an over/under score for a portion of the round of golf, the portion of the round of golf including at least two holes of the golf course; (b) a fairway percentage for the round of golf, the fairway percentage indicating the user's rate of success in placing a golf ball in a fairway of the golf course at a start of each hole; (c) a total number of greens in regulation; (d) a total number of saves from a sand trap of the golf course; (e) a total number of penalty shots; and (f) a handicap calculation for the user.

8. The wristwatch according to claim 6, wherein the memory includes a plurality of memory locations, each memory location for storing a plurality of inputted golf parameters relevant to a different golf course.

9. The wristwatch according to claim 1, wherein the memory includes a plurality of memory locations, each memory location for storing a plurality of inputted golf parameters relevant to a separate round of golf, and wherein the processor is adapted to compute and present on the display at least one calculated average statistic for the plurality of separate rounds of golf.

* * * * *